(12) United States Patent
Key et al.

(10) Patent No.: US 12,724,020 B2
(45) Date of Patent: Sep. 1, 2026

(54) WATER QUALITY MONITOR SYSTEM AND METHOD

(71) Applicant: Pentair Water Pool and Spa, Inc., Cary, NC (US)

(72) Inventors: Adam Key, Cary, NC (US); Mitchell Bellamy, Sanford, NC (US); Drake Fisher, Hickory, NC (US)

(73) Assignee: Pentair Water Pool and Spa, Inc., Cary, NC (US)

( * ) Notice: Subject to any disclaimer, the term of this patent is extended or adjusted under 35 U.S.C. 154(b) by 0 days.

(21) Appl. No.: 18/457,308

(22) Filed: Aug. 28, 2023

(65) Prior Publication Data

US 2023/0400445 A1 Dec. 14, 2023

Related U.S. Application Data

(63) Continuation of application No. 16/801,434, filed on Feb. 26, 2020, now Pat. No. 11,754,545.

(Continued)

(51) Int. Cl.

*G01N 33/18* (2006.01)
*G01K 3/00* (2006.01)

(Continued)

(52) U.S. Cl.

CPC ......... *G01N 33/1886* (2013.01); *G01K 3/005* (2013.01); *G01K 7/22* (2013.01);

(Continued)

(58) Field of Classification Search

CPC ........... G01N 33/1886; G01N 27/4167; G01N 27/4168; G01N 33/1893; G01K 3/005;

(Continued)

(56) References Cited

U.S. PATENT DOCUMENTS

D138,325 S 7/1944 Pool
3,162,470 A 12/1964 Davidson et al.

(Continued)

FOREIGN PATENT DOCUMENTS

CA 2224789 A1 6/1998
CN 207215807 U 4/2018

(Continued)

OTHER PUBLICATIONS

Communication pursuant to Article 94(3)EPC issued for European Patent Application No. 20159540.2 on Apr. 23, 2024, 6 pages.

(Continued)

*Primary Examiner* — Nathaniel T Woodward
*Assistant Examiner* — Philip L Cotey
(74) *Attorney, Agent, or Firm* — Husch Blackwell LLP

(57) ABSTRACT

A water quality monitor for a swimming pool is disclosed. The water quality monitor has a base having a first end and a second end, a removable cover coupled to and enclosing the first end of the base, a flow cell jar extending from the second end of the base, and a sensor probe connected to the second end of the base and extending downwardly into the flow cell jar. The sensor probe is configured to measure a plurality of water quality parameters. The monitor further includes a debris filter provided in a fluid flow path between an inlet and a first side of the base, and a controller configured to provide a connection between the water quality monitor and a cloud storage system using a wireless network. The measured plurality of water quality parameters are transmitted through the wireless network to the cloud storage system.

19 Claims, 3 Drawing Sheets

Related U.S. Application Data

(60) Provisional application No. 62/810,489, filed on Feb. 26, 2019.

(51) Int. Cl.
*G01K 7/22* (2006.01)
*G01K 13/02* (2021.01)
*G01N 27/416* (2006.01)
*C02F 103/42* (2006.01)
*E04H 4/14* (2006.01)
*H04L 67/12* (2022.01)

(52) U.S. Cl.
CPC ......... *G01K 13/02* (2013.01); *G01N 27/4167* (2013.01); *G01N 27/4168* (2013.01); *C02F 2103/42* (2013.01); *C02F 2209/008* (2013.01); *C02F 2209/02* (2013.01); *C02F 2209/04* (2013.01); *C02F 2209/06* (2013.01); *E04H 4/14* (2013.01); *G01K 13/026* (2021.01); *G01N 33/1893* (2013.01); *H04L 67/12* (2013.01)

(58) Field of Classification Search
CPC ........ G01K 7/22; G01K 13/02; G01K 13/026; C02F 2103/42; C02F 2209/008; C02F 2209/02; C02F 2209/04; C02F 2209/06; C02F 1/76; E04H 4/14; H04L 67/12
See application file for complete search history.

(56) References Cited

U.S. PATENT DOCUMENTS

D242,618 S 12/1976 Milo
4,033,871 A * 7/1977 Wall ...................... G05D 21/02 210/756
D254,266 S 2/1980 Tableriou
4,224,154 A 9/1980 Steininger
4,435,095 A 3/1984 Jones et al.
4,510,487 A 4/1985 Wolfe et al.
4,752,740 A 6/1988 Steininger
4,781,810 A 11/1988 Tucker
4,801,886 A 1/1989 Steininger
4,825,207 A 4/1989 Snell
4,900,432 A 2/1990 Arnold et al.
4,940,946 A 7/1990 Nazaryan
5,055,183 A 10/1991 Buchan
5,115,222 A 5/1992 Peralta et al.
5,124,960 A 6/1992 Miller et al.
5,152,610 A 10/1992 Hallett
5,169,236 A 12/1992 Iest
5,189,350 A 2/1993 Mallett
5,326,481 A 7/1994 Alwerud
5,422,014 A * 6/1995 Allen ...................... C02F 1/008 210/743
5,518,635 A 5/1996 Kohlman
D371,824 S 7/1996 Price et al.
5,616,239 A 4/1997 Wendell et al.
5,681,110 A 10/1997 Burzacchi
5,788,826 A 8/1998 Nyberg
5,798,940 A 8/1998 Bratton et al.
5,895,565 A * 4/1999 Steininger ............... C02F 1/008 210/85
5,898,940 A 5/1999 Cameron
5,996,138 A 12/1999 Kentch
6,003,164 A 12/1999 Leaders
6,113,858 A 9/2000 Tang et al.
D432,206 S 10/2000 Stoltz et al.
6,125,481 A 10/2000 Sicilano
D439,313 S 3/2001 Wey et al.
6,223,359 B1 5/2001 Oltmanns et al.
6,225,900 B1 5/2001 Keon et al.
6,228,272 B1 5/2001 Gola
6,238,553 B1 5/2001 Lin
6,253,227 B1 6/2001 Tompkins et al.
6,294,086 B1 9/2001 Reeves
6,309,538 B1 10/2001 Khan
6,340,431 B2 1/2002 Khan
6,476,721 B1 11/2002 Diebold
6,568,264 B2 * 5/2003 Heger ................... G01F 23/266 73/304 C
6,579,446 B1 6/2003 Teran et al.
6,625,824 B1 9/2003 Lutz et al.
6,653,842 B2 11/2003 Mosley et al.
6,697,706 B2 2/2004 Gardner
6,713,298 B2 3/2004 McDevitt et al.
D489,431 S 5/2004 Antunez
6,792,956 B2 9/2004 Bredo et al.
6,900,736 B2 5/2005 Crumb
6,958,693 B2 10/2005 Rothgeb et al.
7,037,038 B1 5/2006 Haski et al.
D526,382 S 8/2006 Thompson
7,094,353 B2 8/2006 Unhoch
7,167,087 B2 1/2007 Corrington et al.
D537,913 S 3/2007 Biberger et al.
7,292,898 B2 11/2007 Clark et al.
D559,943 S 1/2008 Mercer
7,391,333 B2 6/2008 Madden et al.
7,398,138 B2 7/2008 Emery et al.
7,681,436 B2 3/2010 Biberger
7,752,893 B2 7/2010 Biberger
7,938,909 B2 5/2011 Mortimer et al.
7,993,600 B2 8/2011 Doyle et al.
8,281,647 B2 10/2012 Boutet et al.
8,323,486 B2 12/2012 Andrews et al.
8,347,427 B2 1/2013 Klicpera
8,459,100 B2 6/2013 Biberger
9,097,234 B2 8/2015 Breau et al.
9,494,480 B2 11/2016 Klicpera
9,635,442 B1 4/2017 Chen
9,776,888 B1 10/2017 Kurani et al.
9,784,686 B2 10/2017 Clark
9,834,451 B2 12/2017 Miller et al.
9,858,792 B2 1/2018 Fernandes et al.
9,926,207 B2 3/2018 Rodriguez
10,150,680 B1 * 12/2018 Kurani ................... G01N 33/18
10,287,180 B1 * 5/2019 Kurani ...................... C02F 1/66
10,329,784 B1 6/2019 Corwin
10,577,256 B1 * 3/2020 Kurani ...................... C02F 1/66
2001/0045380 A1 11/2001 Khan
2002/0035403 A1 3/2002 Clark et al.
2002/0117430 A1 * 8/2002 Navarro .................. C02F 1/008 210/85
2002/0195403 A1 12/2002 Takeda et al.
2003/0205509 A1 11/2003 Barnes et al.
2003/0227394 A1 12/2003 Rothgeb et al.
2004/0031329 A1 2/2004 Carpenter et al.
2004/0066313 A1 4/2004 Ong et al.
2004/0197229 A1 10/2004 Runyon
2004/0208499 A1 10/2004 Grober
2005/0167345 A1 8/2005 De Wet et al.
2005/0220169 A1 10/2005 McGowan-Scanlon
2005/0225766 A1 10/2005 Hansen et al.
2005/0276724 A1 * 12/2005 Bremauer ........... B01F 35/7174 422/68.1
2005/0279677 A1 12/2005 Lin
2005/0288821 A1 12/2005 Laflamme et al.
2006/0096927 A1 5/2006 Clukies
2006/0241874 A1 10/2006 Carter
2006/0292043 A1 12/2006 Biberger
2007/0219652 A1 9/2007 McMillan
2010/0096338 A1 4/2010 De Wet et al.
2010/0250449 A1 9/2010 Doyle et al.
2010/0300548 A1 * 12/2010 DeVerse ................... E04H 4/14 137/1
2010/0332149 A1 12/2010 Scholpp
2013/0126403 A1 5/2013 Kilawee et al.
2014/0343736 A1 * 11/2014 Meyer ................. G05D 7/0635 700/282
2016/0012705 A1 1/2016 Baret
2017/0215261 A1 * 7/2017 Potucek ............... H05B 47/105
2017/0235318 A1 8/2017 Bright
2017/0248568 A1 8/2017 Yizhack et al.

(56) References Cited

U.S. PATENT DOCUMENTS

| | | | |
|---|---|---|---|
| 2018/0112430 | A1* | 4/2018 | Shalon .................. E04H 4/1281 |
| 2018/0240322 | A1 | 8/2018 | Potucek et al. |
| 2018/0270548 | A1* | 9/2018 | Richter .................... H04Q 9/00 |
| 2018/0284758 | A1 | 10/2018 | Cella et al. |
| 2019/0025273 | A1 | 1/2019 | Brondum et al. |
| 2019/0135657 | A1* | 5/2019 | Yates ...................... E03B 7/075 |
| 2019/0136557 | A1* | 5/2019 | Jensen .................. E04H 4/1272 |
| 2019/0331636 | A1* | 10/2019 | Carrabba ............. G01N 27/403 |
| 2019/0353156 | A1 | 11/2019 | Ward et al. |
| 2019/0390990 | A1* | 12/2019 | Krywyj ..................... G01L 9/04 |
| 2020/0271635 | A1* | 8/2020 | Key ................... G01N 27/4168 |
| 2021/0047853 | A1* | 2/2021 | Gamboa ............... E04H 4/1281 |
| 2021/0140904 | A1* | 5/2021 | Brondum ........... G01N 27/4166 |
| 2021/0298557 | A1 | 9/2021 | Budampati et al. |

FOREIGN PATENT DOCUMENTS

| | | | |
|---|---|---|---|
| CN | 108226411 | A | 6/2018 |
| DE | 19810400 | A1 | 9/1990 |
| DE | 19921436 | A1 | 11/2000 |
| EP | 821514 | A1 | 1/1998 |
| EP | 1847513 | A1 | 10/2007 |
| FR | 2932207 | A1 | 12/2009 |
| KR | 20130048613 | A | 12/2004 |
| KR | 101261553 | B1 | 4/2013 |
| KR | 20040102712 | A | 5/2015 |
| WO | 03087501 | A1 | 10/2003 |
| WO | 03091668 | A2 | 11/2003 |
| WO | 2010051842 | A1 | 5/2010 |
| WO | 2016077322 | A1 | 5/2016 |
| WO | 2017217999 | A1 | 12/2017 |
| WO | 2018198018 | A1 | 11/2018 |

OTHER PUBLICATIONS

Griffin, Wm. R., “Maintaining Swimming Pools, Spas, Whirlpool Tubs and Saunas”, Cleaning Consultant Services, Inc., pp. 1-4, 2001.

“Water Chemistry for Swimming Pools,” North Carolina Department of Environment and Natural Resources, available on the Internet archive at <http://web-archive.org/>, Dec. 19, 2002, 12 pgs.

Examination Report issued for European Patent Application No. 20159540.2 dated Sep. 30, 2022, 7 pages.

Examination Report No. 1 issued by the Australian Patent Office for Australian Patent Application No. 2020201395 dated Sep. 27, 2024, 5 pages.

Examination Report No. 2 issued by the Australian Patent Office for Australian Patent Application No. 2020201395, dated Mar. 3, 2025, 6 pages.

Examination Report issued by the European Patent Application No. 20159540.2 on Sep. 16, 2025, 9 pages.

* cited by examiner

WATER QUALITY MONITOR SYSTEM AND METHOD

RELATED APPLICATIONS

This application is a continuation of U.S. patent application Ser. No. 16/801,434, filed Feb. 26, 2020, which claims priority to U.S. Provisional Patent Application No. 62/810,489, filed on Feb. 26, 2019, the entire contents of which are hereby incorporated by reference.

BACKGROUND

Homeowners may struggle to control the quality of the water in aquatic applications such as swimming pools. (As used throughout, aquatic applications include at least swimming pools, spas, hot tubs, and the like.) The water chemistry may be affected by one or more of environmental factors and weather conditions (e.g., rain, sunlight, hail, wind, pollen, debris, and the like) and human elements (e.g., bacteria, urine, and sweat). In order to account for these factors, a user may adjust the chemical properties of their pool on a weekly (or more frequent basis), which may result in providing too much disinfectant or other chemical agents. Ultimately, water that is out of chemical balance may irritate skin, hair, or clothing. Often, additional chemicals may need to be added to maintain the pH at an acceptable level.

In some known systems, a water quality monitor may be provided in a housing designed to float on the surface of the water of the pool. These systems suffer from numerous drawbacks, however. For example, a floating system may interfere with swimmers or others in the water. Further, the user may need to enter the swimming pool to access the floating system to read the measurements.

SUMMARY

Accordingly, there exists a need for a system and method to provide pool owners and pool servicers with an enhanced system and method for in-line monitoring of water quality parameters.

Some embodiments provide for a water quality monitor system comprising a base having a first end and a second end. A cover is removably coupled to the first end of the base such that the cover surrounds and covers the first end of the base. A flow cell jar is connected to the second end of the base and a sensor probe is connected to the second end of the base and extends downwardly into the flow cell jar. The sensor probe is configured to measure a plurality of water quality parameters. The base further includes an inlet and an outlet connected to opposing ends of the base and connected in-line to the plumbing of a swimming pool recirculation system. A controller is configured to provide a connection between the water quality monitor and a cloud-based storage system, using a wireless network. The measured water quality parameters may be transmitted through the wireless network to the cloud storage system.

In some forms, the plurality of water quality parameters comprises pH, oxidation reduction potential, and temperature. The water quality monitor can be mounted to an equipment pad. The water quality monitor can include a removable antenna. The water quality monitor can include a removable and rechargeable battery pack. The water quality monitor can include an inlet flow control valve in fluid communication with the inlet and an outlet flow control valve in fluid communication with the outlet. The water quality monitor can include a first tube connector and a second tube connector. In some forms, the first tube connector is configured to connect the inlet and the inlet flow control valve to a first side of the base, and the second tube connector is configured to connect the outlet and the outlet flow control valve to a second side of the base. The water quality monitor can include a flow switch, and the water quality monitor can be configured to periodically check the flow switch for water flow through the swimming pool recirculation system. The water quality monitor can include a wake/pair button configured to return the water quality monitor to fully active operation from reduced power consumption upon actuation of the wake/pair button. The wake/pair button can be configured to pair the water quality monitor with an external electronic device upon actuation of the wake/pair button.

Other embodiments provide for a method for remotely monitoring water quality parameters in a pool using a water quality monitor. The method includes the steps of connecting the water quality monitor in-line with a recirculation system of the swimming pool, determining whether there is sufficient flow through the water quality monitor, measuring water quality parameters using a sensor probe, connecting to a wireless internet connection, transmitting the measured water quality parameters through the wireless internet connection to a cloud storage system, and displaying the measured water quality parameters on a web-based application.

In some forms, the method can include notifying a user of one of improper swimming pool function or proper swimming function. The method can include receiving information about a size of the swimming pool. The method can include periodically rechecking whether there is sufficient fluid flow through the water quality monitor. The method can include periodically rechecking whether there is sufficient fluid flow through the water quality monitor is performed at least once every 15 minutes. The plurality of water quality parameters can include pH, oxidation-reduction potential, and temperature. The method can include receiving a predetermined set of values defined for one or more of pH, oxidation-reduction potential, and temperature. The method can include comparing, at the cloud-based storage system, one or more of measured pH, oxidation-reduction potential, or temperature to the predetermined set of values defined for one or more of pH, oxidation-reduction potential, and temperature. The method can include displaying the comparison of the plurality of water quality parameters to the set of predetermined values. The method can include periodically reconnecting to the wireless internet connection to transmit the plurality of water quality parameter through the wireless internet connection to the cloud storage system.

In one embodiment, a water quality monitor for a swimming pool is disclosed. The water quality monitor includes a base having a first end and a second end, a removable cover coupled to and enclosing the first end of the base, a flow cell jar extending from the second end of the base, and a sensor probe connected to the second end of the base and extending downwardly into the flow cell jar. The sensor probe may be configured to measure a plurality of water quality parameters. The water quality monitor further may include an inlet in communication with a first side of the base and an outlet in communication with a second side of the base. The inlet and outlet may be designed to be connected in-line to plumbing of the swimming pool. The water quality monitor also may include a debris filter provided in a fluid flow path between the inlet and the first side of the base, and a controller configured to provide a connection between the water quality monitor and a cloud storage system using a wireless network, wherein the measured plurality of water quality parameters are transmitted through the wireless network to the cloud storage system.

In some forms, the plurality of water quality parameters includes one or more of pH, oxidation-reduction potential, or temperature. The water quality monitor can be mounted in a vertical orientation on an equipment pad. The water quality monitor can include an intermediate cover between the cover and the base. Further, in some forms, the water quality monitor includes a power assembly coupled to at least one of the base, the intermediate cover, or the cover. The power assembly is removable and is provided in the form of a rechargeable battery pack. The water quality monitor may include an inlet flow control valve in fluid communication with the inlet, and an outlet flow control valve in fluid communication with the outlet. Also, the water quality monitor can include a first tube connector configured to connect the inlet and the inlet flow control valve to the first side of the base, and a second tube connector configured to connect the outlet and the outlet flow control valve to the second side of the base. The sensor probe can be surrounded by the flow cell jar, and the flow cell jar can be designed to hold water that is undergoing testing by the sensor probe. The controller further may comprise a flow switch and the water quality monitor is configured to periodically check the flow switch for water flowing through the plumbing of the swimming pool. The flow switch is configured to instruct the water quality monitor to enter a sleep mode when the flow switch detects little water flow or no water flow within the water quality monitor. Also, the water quality monitor is configured to measure the plurality of water quality parameters at predefined time intervals when water is flowing through the water quality monitor. The water quality monitor can include a wake/pair button configured to return the water quality monitor to fully active operation from a deactivated or reduced power operation upon actuation of the wake/pair button, and the wake/pair button is configured to pair the water quality monitor with an external electronic device upon actuation of the wake/pair button. The water quality monitor further may include a removable antenna.

In some embodiments, a water quality monitor for an aquatic application is provided, wherein the water quality monitor can be designed to measure water flowing therethrough. The water quality monitor may include a base having a first end and a second end, a cover coupled to and enclosing the first end of the base, a removable and rechargeable power assembly coupled to at least one of the base or the cover, a flow cell jar extending from the second end of the base, and a sensor probe connected to the second end of the base and extending downwardly into the flow cell jar. The sensor probe can be configured to measure water quality parameters including a pH value, an oxidation-reduction potential value, and a water temperature value of the water flowing through the water quality monitor. The water quality monitor also can include an inlet with an inlet flow control valve and an outlet on opposing ends of the base and designed to be connected in-line to the plumbing of the aquatic application. The water quality monitor further can include a controller configured to transmit the measured water quality parameters from the water quality monitor to a cloud storage system using a wireless network.

In some forms, the measured water quality parameters may be compared to a predetermined set of parameters at the cloud storage system. Also, the comparison of the measured water quality parameters and the predetermined set of parameters can be displayed on a web-based application.

Other embodiments provide for a method for remotely monitoring water quality parameters in a swimming pool using a water quality monitor. The method includes connecting an inlet and an outlet of the water quality monitor in-line with a recirculation system of the swimming pool, determining whether there is sufficient fluid flow through the water quality monitor, measuring a plurality of water quality parameters using a sensor probe, connecting the water quality monitor to a wireless internet connection, and transmitting the plurality of water quality parameters through the wireless internet connection to a cloud storage system.

DETAILED DESCRIPTION

Figure 1:
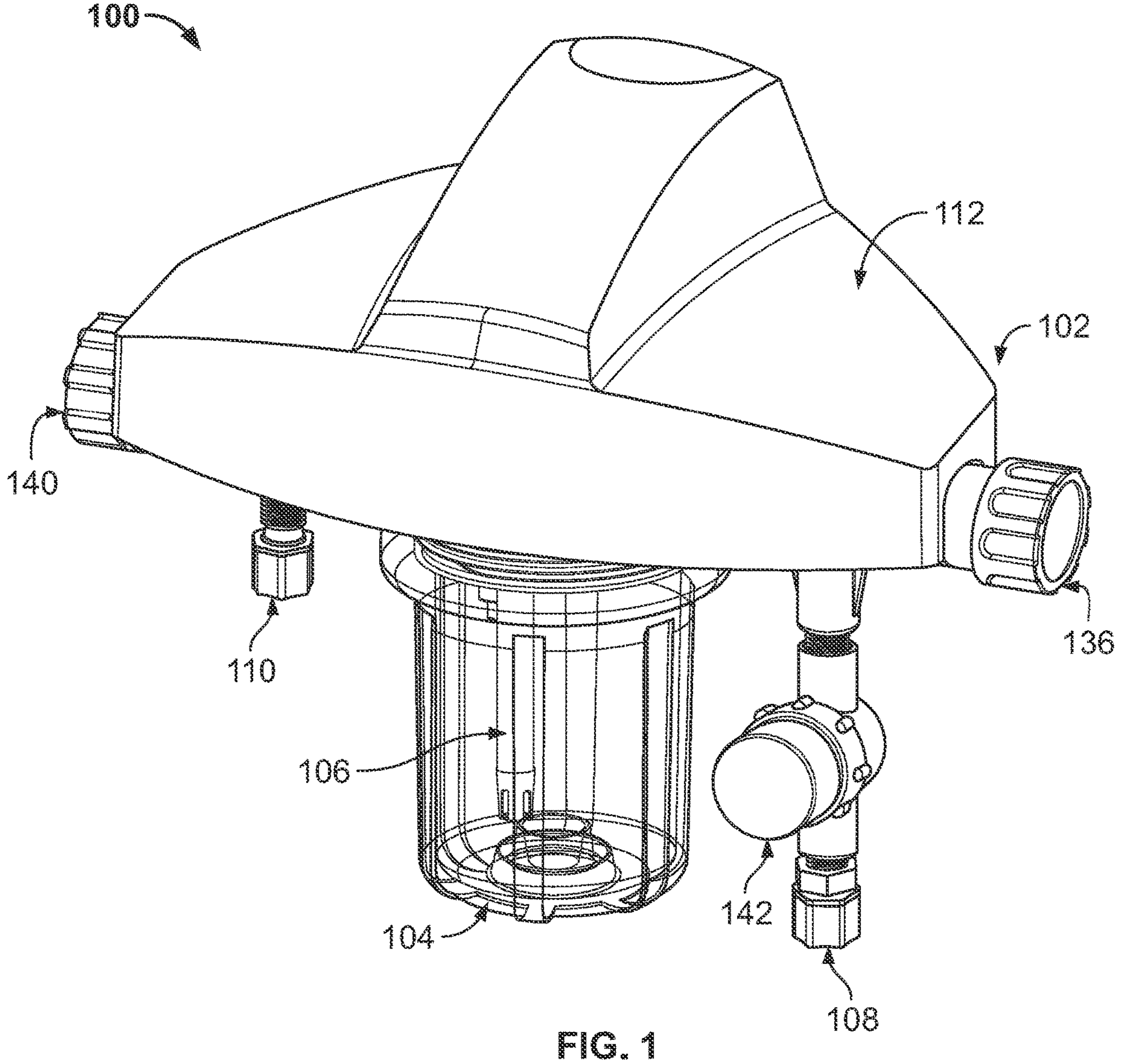
FIG. 1 is an isometric view of a water quality monitor system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of “including,” “comprising,” or “having” and variations thereof herein is meant to encompass the items listed thereafter and equivalents thereof as well as additional items. Unless specified or limited otherwise, the terms “mounted,” “connected,” “supported,” and “coupled” and variations thereof are used broadly and encompass both direct and indirect mountings, connections, supports, and couplings. Further, “connected” and “coupled” are not restricted to physical or mechanical connections or couplings.

As used herein, unless otherwise specified or limited, “at least one of A, B, and C,” and similar other phrases, are meant to indicate A, or B, or C, or any combination of A, B, and/or C. As such, this phrase, and similar other phrases can include single or multiple instances of A, B, and/or C, and, in the case that any of A, B, and/or C indicates a category of elements, single or multiple instances of any of the elements of the categories A, B, and/or C.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 2:
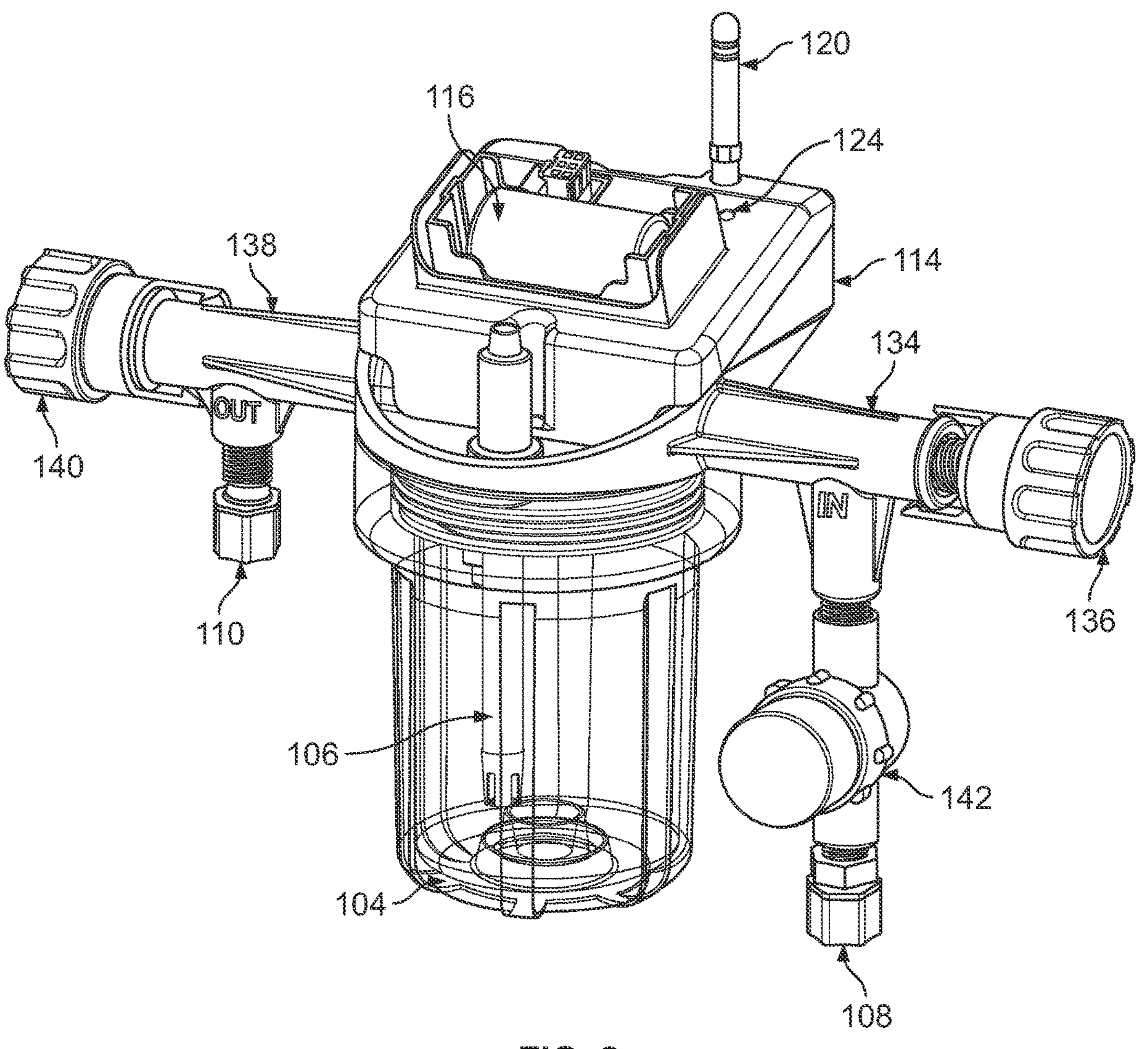
FIG. 2 is an isometric view of the water quality monitor system of FIG. 1, with the cover removed for clarity.
Figure 3:
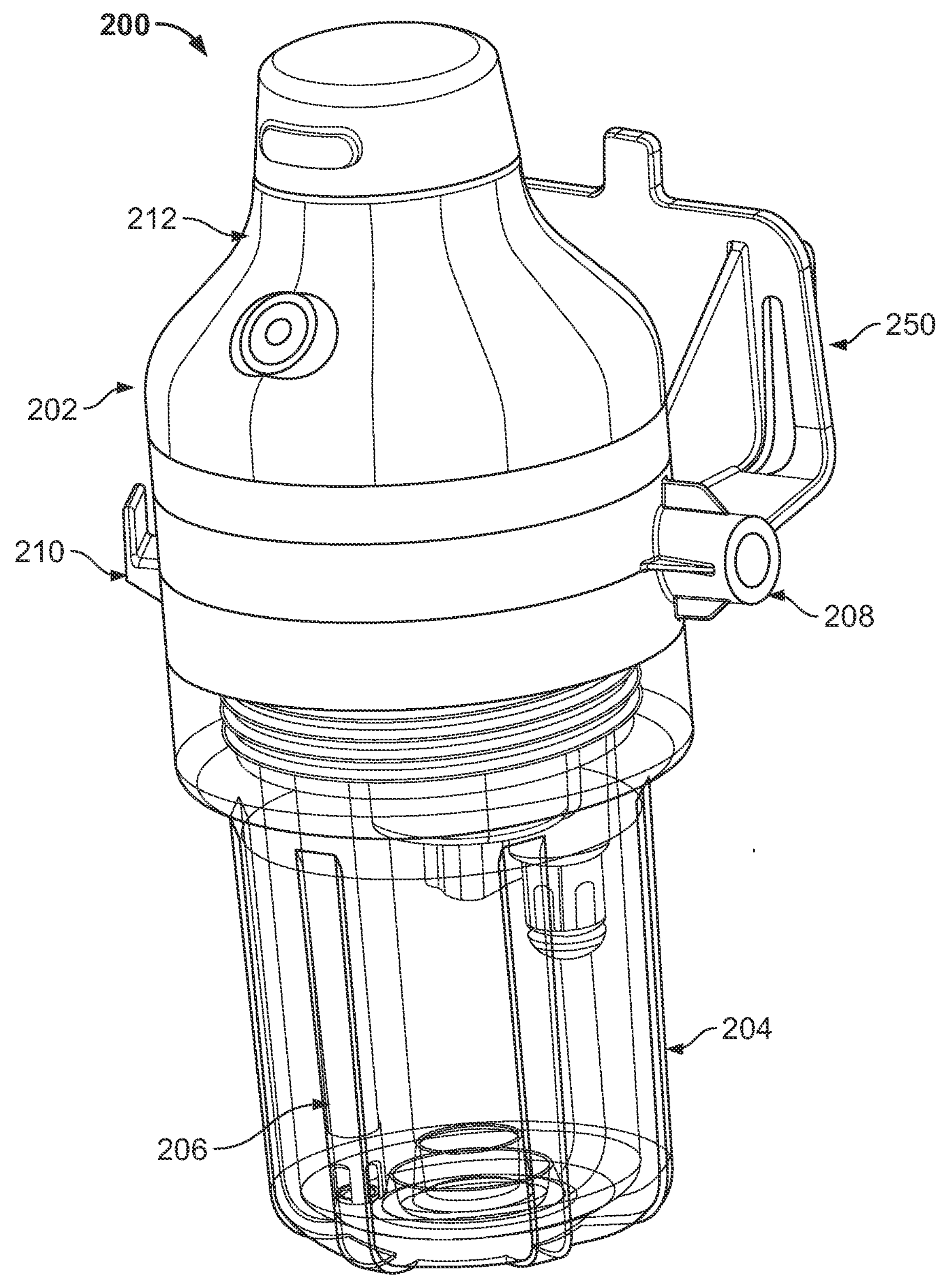
FIG. 3 is an isometric view of a water quality monitor system according to another embodiment.

FIGS. 1-3 illustrate a water quality monitor system 100, according to some embodiments. The water quality monitor 100 is configured and designed to monitor water quality parameters of a residential or commercial aquatic fluid system (such as a swimming pool, spa, hot tub, and other applications where a body of water is confined by a barrier). The water quality monitor 100 is designed to report a water quality status and/or one or more water quality parameters based on measurements of the water quality parameters, to a user. In some embodiments, the measured water quality parameters may include one or more of pH, oxidation-reduction potential (ORP), temperature, and/or other water parameters, and combinations thereof. In one embodiment, the water quality monitor 100 measures pH, ORP, and temperature and may utilize a single probe to do so. The measurements may be taken at a predefined time period (e.g., about every 5 minutes, about every 10 minutes, about every 15 minutes) and transmitted to a user.

FIG. 1 illustrates the water quality monitor system 100 that may be provided in the form of a base 102, a flow cell jar 104, a sensor probe assembly 106, a water inlet 108, and a water outlet 110. The base 102 may include a removable cover 112 configured to protect the internal components of the water quality monitor 100 from environmental conditions. The base 102 and cover 112 may comprise any shape, configuration and/or cross section (e.g., the base 102 and cover 112 may be oblong shaped as depicted in FIGS. 1 and 2 or conically tapered as depicted in FIG. 3).

The cover 112 may be removably coupled to the base 102. For example, the cover 112 may be completely detachable from the base 102 of the water quality monitor. In other embodiments, the cover 112 may be hingedly attached at one end to the base 102 such that the cover 112 may be rotated about a hinge or other pivot point. In this case, the cover 112 may be attached to the base 102 at a rear end, allowing the user to move the cover 112 from a closed position to an open position without fully detaching the cover 112. In other embodiments, the cover 112 may be attached to the base 102 via threads or through an interference fit. During normal operation of the water quality monitor, the cover 112 is in the closed position. The cover 112 may be manufactured using any material suitable for providing adequate protection from natural elements such as wind and rain. The cover 112 may be attached to the base 102 of the water quality monitor using any suitable means.

FIG. 2 depicts a configuration showing when the cover 112 is moved to the open position, or is completely detached from the water quality monitor. In this configuration, the internal components of the base 102 are exposed. The base 102 may include an intermediate cover 114 having a top side and a bottom side. In some embodiments, one or more portions of the base 102 and/or cover 112 may include a power assembly for providing power to the water quality monitor 100. For example, in some embodiments, the top side of the intermediate cover 114 contains a battery 116 for providing power to the water quality monitor 100. In some embodiments, the battery 116 is a lithium battery. The battery 116 may be single use or may be rechargeable. In some embodiments, the rechargeable battery 116 may have a battery life of at least one year. In other embodiments, the rechargeable battery 116 has a battery life of at least 2 years. The system may measure the battery life periodically during operation (e.g., the period may be set to measure battery life about once per hour, once per day, once per week, or some other pre-defined time period). The battery 116 also may be removed from the base 102 for replacement or for recharging and may be purchased where any commonly available batteries are sold. In other embodiments, the battery 116 may be custom made and not commonly available.

In other embodiments, the power supply to the water quality monitor system 100 may be hard wired and/or designed to integrate with another pool component. For example, the power supply may be hard wired to an external controller and/or other automation equipment. In one embodiment, the power supply for the water quality monitor system 100 may be integrated into the power supply of the external controller (e.g., EasyConnect or IntelliConnect). The power supply may also be configured to connect directly to a conventional power outlet, providing, for example, a nominal voltage of 120V.

The water quality monitor 100 also includes an antenna 120 and an antenna cable (not pictured) attached to the top side of and protruding from the intermediate cover 114. In some embodiments, the antenna 120 may be removable and mounted on other portions of the base 102. In other embodiments, the antenna 120 is externally mounted away from the water quality monitor 100. The removable antenna 120 may be protected under the cover 112, but can be removed and an extension cable (not pictured) can be installed to allow relocation of the antenna 120 away from the water quality monitor 100.

Still referring to FIG. 2, the water quality monitor 100 may also include a wake/pair button 124 arranged on the intermediate cover 114 configured to return the water quality monitor 100 to fully active operation from a "sleep mode", which comprises reduced functionality or power consumption, or to pair the water quality monitor 100 with an external electronic device when the button is pressed by the user. The wake/pair button 124 may also include an LED component and an internal factory reset button. In some embodiments, the water quality monitor 100 may also include a flow indicator (not shown) and a flow indicator cover.

The water quality monitor 100 may also include a controller (not shown) in communication with the base 102 and configured to connect the water quality monitor 100 to a cloud based storage system using a wireless network. The controller may comprise a printed circuit board assembly (not shown) configured to connect one or more electronic components of the water quality monitor 100. The printed circuit board assembly may include a Wi-Fi/Bluetooth chipset. In some embodiments, the chipset may be ESP32 and may be compatible with Amazon web services.

The controller may also include a flow switch configured to communicate an operational status to the device when adequate flow is occurring. In some embodiments, the flow switch may be a magnetic reed switch. The water quality monitor 100 may "wake up" periodically to check for water flow through the system. If there is flow, the water quality monitor 100 will record measurements of one or more water quality parameters. If there is no flow, or too little flow, the water quality monitor 100 will return to "sleep" until the beginning of another period. The flow measurements may be taken at a predefined time period (e.g., about every 5 minutes, about every 10 minutes, about every 15 minutes). The controller may also be configured to determine whether the system is electrically coupled to a conventional power outlet and power the water quality monitor 100 with one of the battery 116 or the conventional power outlet accordingly.

FIG. 2 depicts the sensor probe 106 protruding away from the bottom end of the base 102 and extending into and being surrounded by the flow cell jar 104. The sensor probe 106 is configured to measure the water quality parameters of water flowing through the water quality monitor 100. In some embodiments, the sensor probe 106 may be provided as a single probe that is designed to measure one or more of the pH value of the water, the oxidation-reduction potential of the water, water temperature, and combinations thereof. In one embodiment, the sensor probe 106 is a single 3-in-1 probe configured to measure the pH, ORP, and water temperature of the water flowing through the system.

In some forms, the sensor probe 106 includes a pH electrode having two half cells to detect pH, a glass pH ball at the end of the probe, and a reference electrode within the body of the probe. The pH electrode measures the unknown hydrogen ion content of the water with the use of a known hydrogen ion content reference solution.

The sensor probe 106 also includes an ORP sensor that is designed to measure the oxidative activity of dissolved agents. In some embodiments, the dissolved agents may be dissolved oxygen. The ORP sensor may be made of silver, which loses electrons to the oxidizer. The voltage ORP level may be directly correlated to how much oxidizer is in the solution. The sensor probe 106 may also include a silver salt gel solution within the probe. The silver salt gel solution is used as a reference of known ORP. The ORP of the water flowing through the water quality monitor 100 may be calculated by determining the oxidation level of the water with the use of the known ORP of the silver salt gel solution oxidation level. In some embodiments, the silver salt is silver chloride.

The sensor probe 106 may also include a temperature sensor for measuring the water temperature. In some embodiments, the temperature sensor may be a resistor that changes resistance depending on its environmental temperature. In some embodiments, the temperature sensor may be a NTC-10k type thermistor.

The sensor probe 106 extends from the bottom end of the base 102 into the flow cell jar 104. The flow cell jar 104 is designed to hold water that is undergoing testing by the sensor probe 106. In some instances, the flow cell jar 104 is transparent or translucent to allow viewing of the sensor probe 106 and water that is being tested, without removing the flow cell jar 104 from the base 112. The flow cell jar 104 may be provided in the form of a cylindrical cup that is designed to be releasably attached to the base 102. For example, the base 102 and the flow cell jar 104 may comprise separate elements that are coupled together using conventional coupling techniques (e.g., threads, interference fit, tongue and grove, or other joining mechanisms). In other embodiments, the base 102 and the flow cell jar 104 may be manufactured as a single unit. The flow cell jar 104 may comprise any shape, configuration and/or cross section. The flow cell jar 104 may also include a drain plug (not shown) configured to allow water to be removed from the flow cell jar 104.

The base 102 of the water quality monitor 100 is in communication with an external water source through a water inlet 108 and a water outlet 110. The inlet 108 and outlet 110 are configured to allow water to pass through the water quality monitor system 100. The inlet 108 is in fluid communication with a first tube connector 134 and an inlet flow control valve 136. The outlet 110 is in fluid communication with a second tube connector 138 and an outlet flow control valve 140. In some embodiments, the first and second tube connectors 134, 138 have a t-shaped configuration. The first tube connector 134 is configured to connect the inlet 108 and the inlet flow control valve 136 to a first side of the base 102 and the second tube connector 138 is configured to connect the outlet 108 and the outlet flow control valve 140 to a second side of the base 102.

A debris filter 142 may be provided within the fluid flow path between the inlet 108 and the first side of the base 102. The debris filter 142 is designed to collect debris in the water, allowing for unimpeded flow of water through the water quality monitor 100. As illustrated in FIGS. 1 and 2, the water inlet 108 and the water outlet 110 may protrude downwardly from the bottom end of the base 102.

The water quality monitor 100 is designed to be connected in-line to the plumbing of a pool or aquatic system (e.g., a pool pump, a pool filter, and the like) and is in fluid communication with an external water source. Once the water quality monitor 100 is incorporated into the fluid flow path (e.g., pool return line) of the swimming pool recirculation system, water flows into the water quality monitor 100 at the inlet 108 and passes through the flow cell jar 104. The water then moves from the flow cell jar 104 and out of the system through the outlet 110.

In some embodiments, the water quality monitor 100 may be mounted to a vertical surface. For example, the water quality monitor 100 may be mounted to an equipment pad out of the reach of children and may not be readily visible to the user. In some embodiments, the tubing may be attached or otherwise secured by being strapped on to the pipe. In other embodiments, the water quality monitor 100 may be attached using any attachment method.

FIG. 3 illustrates a water quality monitor system 200 that is substantially similar to the embodiment depicted in FIG. 1, except for the differences discussed below. The water quality monitor 200 may generally include a base 202, a flow cell jar 204, and a sensor probe 206. The base 202 may include a tapered conical cover 212. A top portion of the base 202 and the cover 212 may be substantially the same shape such that the cover 212 fits over and encloses the top portion of the base 202. The water quality monitor 200 may further include a water inlet 208 and a water outlet 210 that do not include tube connectors. Instead, the inlet 208 and outlet 210 may be directly connected to the base 202. As further illustrated in FIG. 3, the water quality monitor 200 may include a mount 250 disposed on the back side of the base that is configured to provide support for the water quality monitor while it is mounted.

In use, the water quality monitor 100, 200 may be configured to wake itself from sleep mode every 15 minutes to check for flow through the use of a magnetic reed switch. If there is no flow, or the flow is too low, the water quality monitor 100, 200 will return to sleep mode. Once adequate flow has been established, the water quality monitor 100, 200 will measure one or more water quality parameters of the water system. In some embodiments, the water quality parameters are water temperature, pH, and ORP. The data associated with the water quality parameters may be collected and sent to a cloud environment to be accessed by a web-based browser interface. The web-based browser interface may include one or more of Android, IOS, and other web based browser interfaces.

The water quality monitor 100, 200 may periodically establish an internet connection in order to collect data and report data. In some embodiments, the water quality monitor 100, 200 may connect to the internet every 2 hours and report the last two hours' worth of collected data. In other embodiments, the water quality monitor 100, 200 may report the collected data every hour. The data may be transmitted by using a Wi-Fi connection via a router and the user may access the data using a web based application (App). The App may be designed to notify the user that the aquatic system (e.g., pool) is functioning properly or if it needs attention. The user may see the water temperature, pH, and ORP level associated with color indication of status of each component. In some embodiments, the App will notify the user that their water system is functioning properly or if the water system is in need of attention. During initial set-up of the App, the user may input additional information such as the size of the residential or commercial aquatic fluid system and/or chlorine levels. Inputting the additional information may allow the App to provide the user with recommended actions to take, based on the measured water quality parameters.

In some embodiments, a predetermined set of values is defined for one or more of the water temperature, pH, and ORP level into the cloud based storage system. The data collected by the water quality monitor 100, 200 can be transmitted to the cloud-based storage system, and a comparison of the data to the predetermined set of values can be performed at the cloud based storage system. The user may then access the result of this comparison via the App, where the comparison can be displayed to the user.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

The invention claimed is:

1. A water quality monitor for a swimming pool, comprising:

a base having a first end and a second end;

a removable cover coupled to and enclosing the first end of the base;

a flow cell jar extending from the second end of the base;

a sensor probe connected to the second end of the base and extending downwardly into the flow cell jar, the sensor probe configured to measure a plurality of water quality parameters;

an inlet in communication with a first side of the base and an outlet in communication with a second side of the base, the inlet and outlet designed to be connected in-line to plumbing of the swimming pool;

a debris filter provided in a fluid flow path between the inlet and the first side of the base; and a controller configured to:

provide a connection between the water quality monitor and a cloud storage system using a wireless network;

periodically check for water flow through the water quality monitor; and instruct the water quality monitor to enter a sleep mode when less than a threshold amount of water flow is detected, wherein the measured plurality of water quality parameters are transmitted through the wireless network to the cloud storage system.

2. The water quality monitor of claim 1, wherein the plurality of water quality parameters includes one or more of pH, oxidation-reduction potential, or temperature.

3. The water quality monitor of claim 1, wherein the water quality monitor is mounted in a vertical orientation on an equipment pad.

4. The water quality monitor of claim 1, further comprising an intermediate cover between the cover and the base.

5. The water quality monitor of claim 4, further comprising a power assembly coupled to at least one of the base, the intermediate cover, or the cover.

6. The water quality monitor of claim 5, wherein the power assembly is removable and is provided in the form of a rechargeable battery pack.

7. The water quality monitor of claim 1, further comprising an inlet flow control valve in fluid communication with the inlet, and an outlet flow control valve in fluid communication with the outlet.

8. The water quality monitor of claim 7, further comprising a first tube connector configured to connect the inlet and the inlet flow control valve to the first side of the base.

9. The water quality monitor of claim 7, further comprising a second tube connector configured to connect the outlet and the outlet flow control valve to the second side of the base.

10. The water quality monitor of claim 1, wherein the sensor probe is surrounded by the flow cell jar, and the flow cell jar is designed to hold water that is undergoing testing by the sensor probe.

11. The water quality monitor of claim 1, wherein the controller further comprises a flow switch and the controller is configured to periodically check the flow switch for water flowing through the plumbing of the swimming pool.

12. The water quality monitor of claim 11, wherein the sleep mode comprises reducing functionality of the water quality monitor.

13. The water quality monitor of claim 1, wherein the water quality monitor is configured to measure the plurality of water quality parameters at predefined time intervals when water is flowing through the water quality monitor.

14. The water quality monitor of claim 1, further comprising a wake/pair button configured to return the water quality monitor to fully active operation from a deactivated or reduced power operation upon actuation of the wake/pair button.

15. The water quality monitor of claim 14, wherein the wake/pair button is configured to pair the water quality monitor with an external electronic device upon actuation of the wake/pair button.

16. The water quality monitor of claim 1, further comprising a removable antenna.

17. A water quality monitor for an aquatic application, the water quality monitor designed to measure water flowing therethrough and comprising:

a base having a first end and a second end;

a cover coupled to and enclosing the first end of the base;

a removable and rechargeable power assembly coupled to at least one of the base or the cover;

a flow cell jar extending from the second end of the base;

a sensor probe connected to the second end of the base and extending downwardly into the flow cell jar, the sensor probe configured to measure water quality parameters including a pH value, an oxidation-reduction potential value, and a water temperature value of the water flowing through the water quality monitor;

an inlet with an inlet flow control valve and an outlet on opposing ends of the base and designed to be connected in-line to the plumbing of the aquatic application; and a controller configured to transmit the measured water quality parameters from the water quality monitor to a cloud storage system using a wireless network, the controller further comprising a flow switch configured to periodically check for water flow, wherein the controller instructs the water quality monitor to enter a sleep mode when less than a threshold amount of water flow is detected.

18. The water quality monitor of claim 17, wherein the measured water quality parameters are compared to a predetermined set of parameters at the cloud storage system.

19. The water quality monitor of claim 18, wherein the comparison of the measured water quality parameters and the predetermined set of parameters are displayed on a web-based application.

* * * * *